United States Patent [19]

Baran

[11] 4,417,576
[45] Nov. 29, 1983

[54] DOUBLE-WALL SURGICAL CUFF

[76] Inventor: Ostap E. Baran, 219 E. 12th St., New York, N.Y. 10003

[21] Appl. No.: 352,124

[22] Filed: Feb. 25, 1982

[51] Int. Cl.³ .......................................... A61M 25/00
[52] U.S. Cl. ................................ 128/207.15; 604/101
[58] Field of Search ............... 128/207.15, 349 B, 260; 604/96, 101

[56] References Cited

U.S. PATENT DOCUMENTS

| 3,173,418 | 3/1965 | Baran | 128/207.15 |
| 3,348,542 | 10/1967 | Jackson | 128/207.15 |
| 3,638,655 | 2/1972 | Doherty | 128/207.15 |
| 3,640,282 | 2/1972 | Kamen et al. | 128/207.15 |
| 4,209,014 | 6/1980 | Sefton | 128/214 F |

FOREIGN PATENT DOCUMENTS 2012596  8/1979  United Kingdom ........... 128/207.15

Primary Examiner—Henry J. Recla
Attorney, Agent, or Firm—S. C. Yuter

[57] ABSTRACT

A surgical cuff for introduction into a body passage such as a trachea of a surgical fluid such as an anesthetic comprises a tubular base member with an imperforate inflatable tubular inner cuff member encircling the tubular base member and a distensible tubular outer cuff member encircling the inner cuff member. The outer cuff member is multiperforated at spaced points. A sponge-like material, like sponge rubber, is positioned in the space between the inner and outer cuff members. Separate passages communicate with the space occupied by the sponge-like material and the space between the tubular base member and the inner cuff member. Surgical fluid such as an anesthetic is introduced into the space with the sponge-like material, which absorbs it. Then air is pumped into the space between the tubular base member and the inner cuff member to expand the inner cuff member and, thus, compress the sponge-like material to drive the absorbed surgical fluid through the perforations in the wall of the outer cuff member to the adjacent walls of the body passage.

7 Claims, 4 Drawing Figures

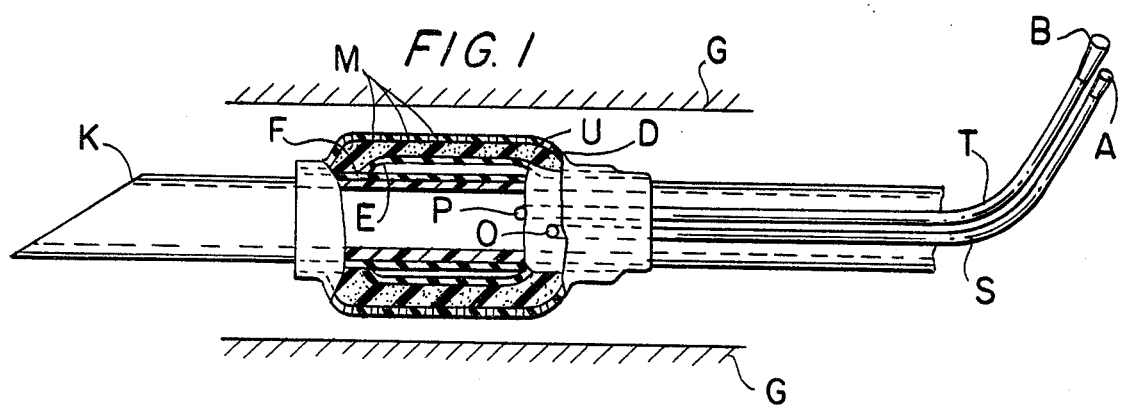
FIG. 1
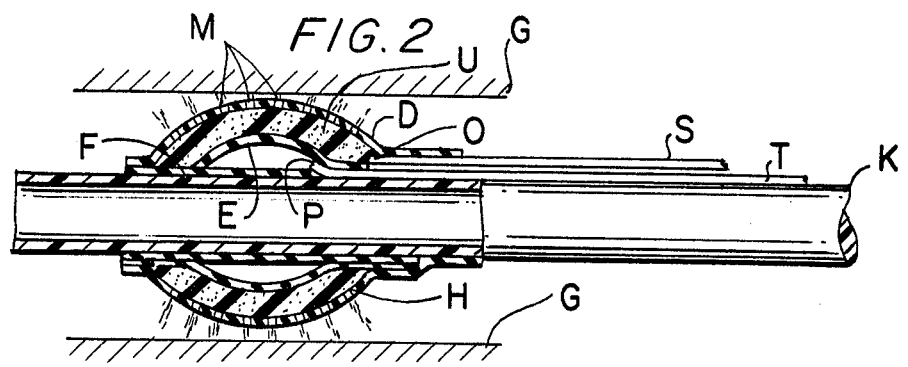
FIG. 2
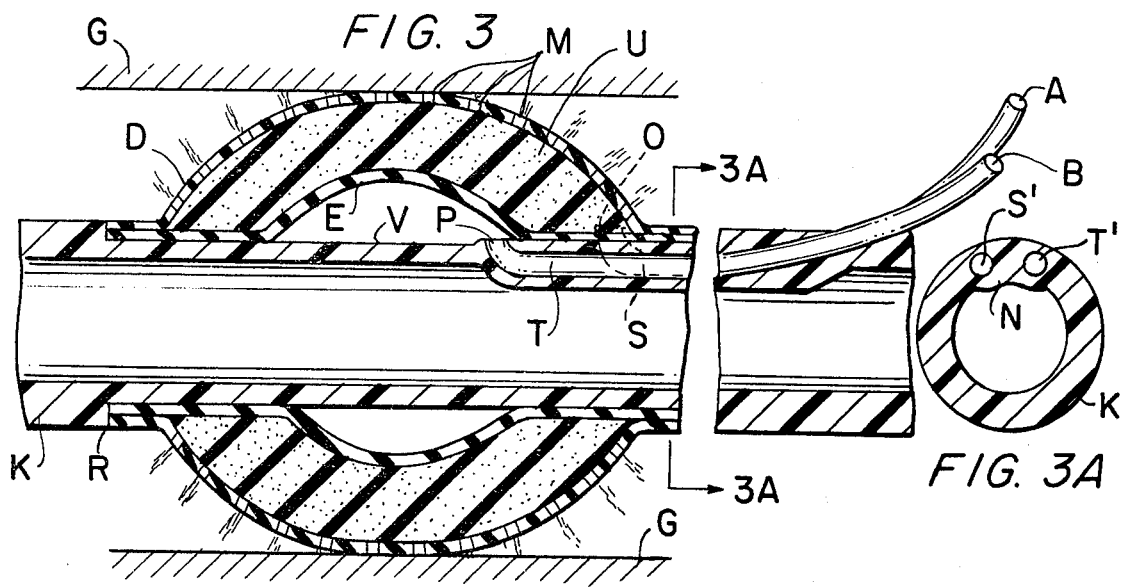
FIG. 3
FIG. 3A

DOUBLE-WALL SURGICAL CUFF

FIELD OF THE INVENTION

This invention relates to improved surgical cuffs and, more particularly, to an improved double-wall endotracheal cuff which is the subject of my U.S. Pat. No. 3,173,418 issued Mar. 16, 1965 ("my 1965 patent").

BACKGROUND OF THE INVENTION

The invention disclosed in my 1965 patent relates to a double-wall endotracheal cuff, the external wall of which is multiperforated for the administration of continuous or intermittent local endotracheal anesthesia. The very same cuff may be very advantageously employed for endo-esophageal, endo-stomach, endo-duodenal, or pharyngeal surface anesthesia as well as surface anesthesia in any other cavity in the body, as well as for other necessary medicaments.

The problem which anesthetists and surgeons have encountered in the use of endotracheal anesthesia, and which the invention of my 1965 patent solved, is that shortly (about three quarters of an hour or sooner) after injection of anesthetic into the trachea and placing of the endotracheal tube, the anesthetic wears off or is destroyed and the patient is thereafter unable to endure the presence of the tube in the trachea. The patient starts to cough and vomit, making it difficult for the surgeon to perform the operating procedure. Attempts had been made, prior to the invention of my 1965 patent, to solve this problem by use of deep anesthesia administered to such level that the patient loses all endotracheal feeling and reflexes. Frequently this unnecessarily intoxicated the whole body system and often endangered the life of the patient, especially in the presence of damage to the cardio-vascular system, liver, kidney, lungs or brain centers.

The invention of my 1965 patent is a double-wall endotracheal cuff for continuous or intermittent local endotracheal anesthesia around the endotracheal tube which enables the patient to tolerate the endotracheal tube, not only during the light-superficial stage of general anesthesia but also in the absence of general anesthesia when the patient is awake. My invention could be life saving in conditions such as tetanus or bilateral pneumonia when a continuous free passage of oxygen to the lungs and suction of exudate from the lungs represents most important factors for a succesful recovery.

While the invention of my 1965 patent was a major improvement in the anesthetic art it did not solve all of the problems. One problem which became known shortly after the invention went into surgical use was that local anesthetic injected around the wall of the outer cuff was metabolized in 45 minutes to an hour and, therefore, a new portion of anesthetic had to be administered. The additional anesthetic created the risk of oversaturating the patient. Thus, there was a long-felt need to solve this problem and its solution eluded me and others until now.

SUMMARY OF THE INVENTION

Thus the principal object of my new invention is to solve the problem presented by the invention of my 1965 patent in requiring a new and possibly oversaturating administration of anesthetic after 45 minutes to an hour.

Another object of the present invention is to provide an improved double-wall surgical cuff.

Still another object of the present invention is to satisfy the two previous objects with a relatively inexpensive modification of the invention of my 1965 patent.

Briefly, these and other objects of my new invention are achieved by a surgical cuff for introduction into a body passage such as a trachea of a surgical fluid such as an anesthetic comprising a tubular base member with an imperforate inflatable tubular inner cuff member encircling the tubular base member and a distensible tubular outer cuff member encircling the inner cuff member. The outer cuff member is multiperforated at spaced points. A sponge-like material, like sponge rubber, is positioned in the space between the inner and outer cuff members. Separate passages communicate with the space occupied by the sponge-like material and the space between the tubular base member and the inner cuff member. Surgical fluid such as an anesthetic is introduced into the space with the sponge-like material, which absorbs it. Then air is pumped into the space between the tubular base member and the inner cuff member to expand the inner cuff member and, thus, compress the sponge-like material to drive the absorbed surgical fluid through the perforations in the wall of the outer cuff member to the adjacent walls of the body passage.

An advantage of the invention is that the inner cuff member may be further expanded to gently (via the sponge-like material) press the wall of the outer cuff member against the adjacent walls of the body passage to close the body passage when that is desirable.

BRIEF DESCRIPTION OF DRAWINGS

Other objects, features and advantages of the present invention will be apparent from the following detailed description of the invention taken together with the accompanying drawings wherein:

FIG. 1 is a side view, partly broken away and in section, of an improved deflated surgical double cuff made in accordance with the invention and shown mounted on an endotracheal tube.

FIG. 2 is a similar view, with the endotracheal tube and cuff rotated 90 degrees from the FIG. 1 position showing the inner cuff in inflated condition and, thus, compressing the sponge-like material between the inner and outer cuffs.

FIG. 3 shows a modification, in accordance with the preferred embodiment of the invention, in an enlarged sectional view showing the improved surgical cuff mounted permanently on an endotracheal tube as an integral unit.

FIG. 3A is a section along the line 3—3 of FIG. 3 showing the passages to the inner cuff and to the sponge-like material between the cuffs as part of the wall of the endotracheal tube.

DETAILED DESCRIPTION OF THE INVENTION

The specification and drawings of my 1965 patent are hereby incorporated by reference, and the corresponding elements in this description are designated by the same reference characters as those of my 1965 patent.

Referring to the improved surgical cuff shown in FIGS. 1 and 2 as a double-wall endotracheal cuff, which is shown inserted in a trachea adjacent the internal wall G of the trachea, internal cuff E encircles endotracheal tube K. External multiperforated cuff D, in turn, encircles internal cuff E. Positioned in the space between internal cuff E and external cuff D is the sponge-like material U, which is preferably sponge rubber although natural sponge and equivalent sponge-type material may also be employed.

Canal T, which has an opening B for the introduction of air, terminates at opening P (FIG. 2) within the space between endotracheal tube K and internal cuff E. Canal S, which has an opening A for the introduction of a surgical fluid such as an anesthetic, terminates at opening O within the space between internal cuff E and external cuff D occupied by the sponge-like material U.

Both internal cuff E and external cuff D are fixed to the basal rubber cylinder F. External cuff D is multiperforated as at M.

Initially anesthetic fluid H is injected into sponge-like material U under enough pressure to saturate material U with enough anesthetic H for a desired surgical procedure. Then air is pumped into opening B to inflate internal cuff E as shown in FIG. 2. As internal cuff E distends it compresses sponge-like material U to inject anesthetic H onto internal wall G of the trachea. The spraying of anesthetic H occurs uniformaly around the tube K and external cuff D, anesthetizing the internal wall G and by gravity flowing into the bronchial tree or upper respiratory airway depending on the position of the patient.

When an additional application of anesthetic is indicated, usually 45 minutes to an hour later, the air pressure through canal T is increased, distending internal cuff D still more to further compress sponge-like material U and administer another application of anesthetic H to the internal wall G of the trachea via perforations M.

More particularly, the procedure for employing my invention is as follows:

After local spraying of the anesthetic into the pharynx and general induction of anesthesia, together with injection of relaxant drugs, and properly oxygenating the patient, the endotracheal tube K with its double walled cuff is inserted into the trachea. Immediately 2 or 3 cc. of Cyclaine or other local anesthetizing agent are injected into the space between the internal cuff E and external cuff D through opening A. Under fluid pressure from the anesthetic absorbed by the sponge-like material U and pressure from the distended internal cuff E due to pumped air, the external cuff D is stretched, the small multiple holes M are opened and the anesthetic H is sprayed through them around the endotracheal tube K and on the endotracheal mucous membrane, flowing down the tracheobronchial tree or into the pharynx according to the position of the patient.

Usually in about 45 minutes to an hour the anesthetic fluid is absorbed or destroyed and the patient may react to the presence of the endotracheal tube K in the trachea. To prevent that reflex, additional air pressure is put on external cuff D to further distend it, further compressing sponge-like material U and the local endotracheal anesthesia is thereby prolonged.

Instead of intermittent administration of anesthetic fluid H it is possible to maintain continuous local endotracheal anesthesia by continuously increasing the air pressure in the air space between internal cuff E and the endotracheal tube K continuously, though slowly, compressing the sponge-like material U.

In this manner there is the possibility not only of continuously maintaining the local anesthesia, but by continuous absorption of the local anesthesia it may be possible through the blood circulation to support general anesthesia by a local anesthetic, thereby avoiding cardio-vascular reflexes. This may be done, for example, by the use of Procaine or Pronestyl during some cardio-vascular operations.

A further advantage of this kind of anesthesia is that local anesthesia of the larynx reduces the danger of laryngo-spasms.

A more important advantage is that local anesthesia is prolonged and, at the same time, less anesthesia is used to improve tolerance of the endotracheal tube after prolonged surgery. Another advantage of the present invention over the invention of my 1965 patent is that inner cuff E may be expanded enough to gently press sponge-like material U and thus external cuff D against the internal wall G of the trachea to close the trachea passage when that is desirable. Sponge-like material U functions like a buffer to smoothly apply pressure to the internal wall G. In the invention of my 1965 patent closing the passage is a critical operation because too little pressure on the inner cuff E results in a failure to close the passage and too much pressure can easily injure the passage wall membrane. The present invention provides much better control and thus reduces the risk of impeding or blocking blood flow and the danger of ischemic necrosis of the mucous membrane.

The preferred embodiment of my improved double-wall surgical cuff is shown in FIGS. 3 and 3A, with corresponding parts designated by the same reference characters as the FIGS. 1, 2 embodiment except for canals S' and T' which are incorporated within the wall of the endotracheal tube K. Moreover, internal cuff E employs the outer surface V of the portion of the tube K encircled by cuff E to complete the space enclosed by cuff E.

In FIG. 3 inner cuff E has been expanded to press external cuff E against the internal wall G of the trachea via sponge-like material U which smooths out the application of the pressure against internal wall G making proper passage closure much easier and more effective.

Those skilled in the art may be able to make other modifications and uses of the illustrated embodiments of my invention and devise other specific structures for incorporating its principles; especially the structures disclosed in my 1965 patent which can be modified to incorporate my present invention, which are not specifically disclosed in this specification. It is to be understood that it is intended to cover all such changes and modifications which do not constitute a departure from the true spirit and scope of the invention.

What I claim is:
1. A surgical cuff for introduction into an integral body passage comprising:
(A) A tubular base member;
(B) An imperforate flexible inflatable tubular inner cuff member having its outer ends connected to said tubular base member;
(C) a flexible distensible tubular outer cuff member having its outer ends connected to said tubular base member, the proximal outer end of said outer cuff member being connected to said tubular base member at a given distance from the proximal outer end of said inner cuff member and the distal outer end of said outer cuff member being connected to said tubular base member at a distance from the distal outer end of said inner cuff member which is substantially the same as said given distance, the wall of said outer cuff member being multiperforated at spaced points;

(D) A sponge-like material in the space between said inner and outer cuff members and adapted to absorb a surgical fluid and then expel said fluid when compressed, said sponge-like material comprising a layer having a substantially uniform thickness;

(E) First passage means communicating with the space between said inner cuff member and outer cuff member for introducing a surgical fluid into said space for absorption for said sponge-like material; and (F) Second passage means communicating with the space between said inner cuff member and said tubular base member for inflating said inner cuff member to displace wall portions thereof toward the wall of said outer cuff member;

(G) Whereby the spacing between the opposed walls of the inner and outer cuff members is reduced to uniformly compress said sponge-like material and thereby transmit absorbed surgical fluid outwardly through the perforations of the wall of said outer cuff member; and (H) Whereby said flexible inner cuff member may be further expanded to gently press said flexible outer cuff member, via said sponge-like material, against the wall of the integral body passage to close the passage; and (I) Whereby said sponge-like material also functions like a buffer and smooths out the application of the pressure against said wall of the body passage and thereby reduces the possibility of ischemic necrosis of the integral body passage; and (J) Whereby when said inner cuff member is deflated said perforations of the wall of said outer cuff member are closed preventing backflow of said surgical fluid and thereby precisely controlling the amount of said surgical fluid transmitted around said outer cuff member.

2. A surgical cuff according to claim 1 wherein the wall of said tubular base member is formed with a pair of passages respectively communicating with the space between said inner and outer cuff members and the space between said inner cuff member and said tubular base member.

3. A surgical cuff according to claim 1 wherein said first and second passage means are respectively first and second canals separate from said tubular base member.

4. A surgical cuff according to claim 2 wherein said inner and outer cuff members are separate from but surround said tubular base member with their outer ends making sealing contact with said tubular base member.

5. A surgical cuff member according to claim 2 wherein the outer surface of said tubular base member forms the inner wall of said inner cuff member.

6. A surgical cuff according to claim 1 wherein said tubular base member is an endotracheal tube.

7. A surgical cuff according to claims 1, 3, 4, 5 or 6 wherein said surgical fluid is an anesthetic and said sponge-like material is adapted to absorb an anesthetic.

* * * * *